United States Patent [19]

Failli et al.

[11] Patent Number: 5,130,307
[45] Date of Patent: Jul. 14, 1992

[54] AMINOESTERS OF RAPAMYCIN

[75] Inventors: Amedeo A. Failli, Princeton Junction; Craig E. Caufield, Plainsboro, both of N.J.; Robert J. Steffan, Langhorne, Pa.

[73] Assignee: American Home Products Corporation, New York, N.Y.

[21] Appl. No.: 657,294

[22] Filed: Feb. 19, 1991

Related U.S. Application Data

[63] Continuation-in-part of Ser. No. 589,878, Sep. 28, 1990, abandoned.

[51] Int. Cl.[5] ............... A61K 31/395; C01D 401/06
[52] U.S. Cl. .................... 514/321; 514/291; 514/183; 340/456; 346/90
[58] Field of Search ............. 540/456; 514/183, 321, 514/291; 546/90

[56] References Cited

U.S. PATENT DOCUMENTS

| | | | |
|---|---|---|---|
| 3,929,992 | 12/1975 | Sehal et al. | 424/122 |
| 3,993,749 | 11/1976 | Sehal et al. | 424/122 |
| 4,316,885 | 2/1982 | Rakhet et al. | 424/122 |
| 4,401,653 | 4/1983 | Eve | 424/122 |
| 4,650,803 | 3/1987 | Stella et al. | 514/291 |
| 4,885,171 | 12/1989 | Surendra et al. | 424/122 |

OTHER PUBLICATIONS

Lancet, 1183 (1978).
Immunology, C. V. Moseby Co., pp. 12.8–12.11 (1989).
Can. J. Physiol. Pharmacol. 55, 48 (1977).
FASEB 3, 3411 (1989).
FASEB 3, 5256 (1989).
J. Antibiot. 28, 721–726 (1975).
J. Antibiot. 28, 727–732 (1975).
J. Antibiot. 31, 539–545 (1978).

Primary Examiner—Robert T. Bond
Attorney, Agent, or Firm—Arnold S. Milowsky

[57] ABSTRACT

A compound of the structure

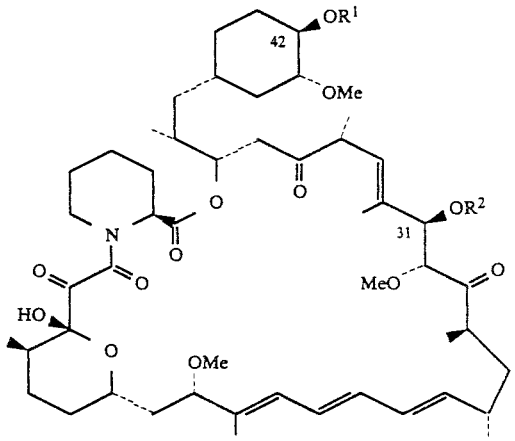

wherein $R^1$ and $R^2$ are each, independently, hydrogen or

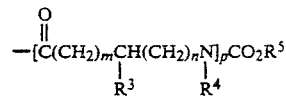

with the proviso that $R^1$ and $R^2$ are not both hydrogen;
$R^3$ is hydrogen, alkyl, aralkyl, $-(CH_2)_qCO_2R^6$, $-(CH_2)_rNR^7CO_2R^8$, carbamylalkyl, aminoalkyl, hydroxyalkyl, guanylalkyl, mercaptoalkyl, alkylthioalkyl, indolylmethyl, hydroxyphenylmethyl, imidazoylmethyl or phenyl which is optionally mono-, di-, or tri-substituted with a sustituent selected from alkyl, alkoxy, hydroxy, cyano, halo, nitro, carbalkoxy, trifluoromethyl, amino, or a carboxylic acid;
$R^4$ and $R^7$ are each, independently, hydrogen, alkyl, or aralkyl;
$R^5$, $R^6$, and $R^8$ are each, indpendently, alkyl, aralkyl, fluorenylmethyl, or phenyl which is optionally mono-, di-, or tri-substituted with a substituent selected from alkyl, alkoxy, hydroxy, cyano, halo, nitro, carbalkoxy, trifluoromethyl, amino, or a carboxylic acid;
m is 0–4;
n is 0–4;
p is 1–2;
q is 0–4;
r is 0–4;
wherein $R^3$, $R^4$, m, and n are independent in each of the

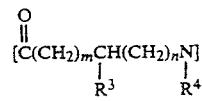

subunits when p=2;
or a pharmaceutically acceptable salt thereof, which by virtue of its immunosuppressive activity is useful in treating transplantation rejection host vs. graft disease, autoimmune diseases, and diseases of inflammation, and by virtue of its antifungal activity is useful in treating fungal infections.

22 Claims, No Drawings

AMINOESTERS OF RAPAMYCIN

This is a continuation in part of application Ser. No. 07/589,878, filed Sep. 28, 1990.

BACKGROUND OF THE INVENTION

This invention relates to novel esters of rapamycin and a method for using them in the treatment of transplantation rejection, host vs. graft disease, autoimmune diseases, diseases of inflammation, and fungal infections.

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Seghal et al., J. Antibiot. 28, 727 (1975); H. A. Baker et al., J. Antibiot. 31, 539 (1978); U.S. Pat. No. 3,929,992; and U.S. Pat. No. 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989), rapamycin has been shown to be effective in inhibiting transplant rejection (U.S. patent application Ser. No. 362,544 filed Jun. 6, 1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); and R. Y. Calne et al., Lancet 1183 (1978)].

Mono- and diacylated derivatives or rapamycin (esterified at the 28 and 43 positions) have been shown to be useful as antifungal agents (U.S. Pat. No. 4,316,885) and used to make water soluble prodrugs of rapamycin (U.S. Pat. No. 4,650,803). Recently, the numbering convention for rapamycin has been changed; therefore according to Chemical Abstracts nomenclature, the esters described above would be at the 31- and 42-positions.

DESCRIPTION OF THE INVENTION

This invention provides derivatives of rapamycin which are useful as immunosuppressive, anti-inflammatory, and antifungal agents having the structure

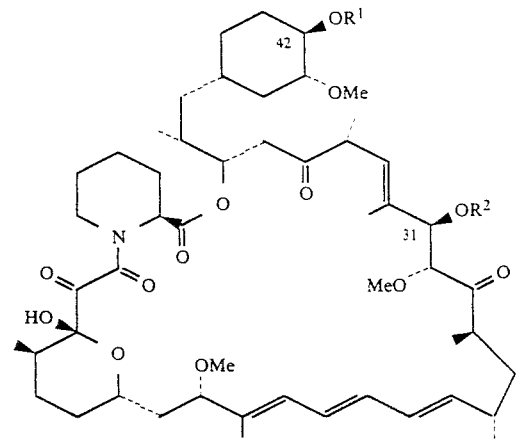

wherein $R^1$ and $R^2$ are each, independently, hydrogen or $$-[C(CH_2)_mCH(CH_2)_nN]_pCO_2R^5$$
$$\phantom{-[C(CH_2)_mCH(CH_2)_n}R^3\phantom{]_p}R^4$$

with the proviso that $R^1$ and $R^2$ are not both hydrogen;
$R^3$ is hydrogen, alkyl of 1-6 carbon atoms, aralkyl of 7-10 carbon atoms, $-(CH_2)_qCO_2R^6$, $-(CH_2)_rNR^7CO_2R^8$, carbamylalkyl of 2-3 carbon atoms, aminoalkyl of 1-4 carbon atoms, hydroxyalkyl of 1-4 carbon atoms, guanylalkyl of 2-4 carbon atoms, mercaptoalkyl of 1-4 carbon atoms, alkylthioalkyl of 2-6 carbon atoms, indolylmethyl, hydroxyphenylmethyl, imidazoylmethyl or phenyl which is optionally mono-, di-, or tri-substituted with a substituent selected from alkyl of 1-6 carbon atoms, alkoxy of 1-6 carbon atoms, hydroxy, cyano, halo, nitro, carbalkoxy of 2-7 carbon atoms, trifluoromethyl, amino, or a carboxylic acid;
$R^4$ and $R^7$ are each, independently, hydrogen, alkyl of 1-6 carbon atoms, or aralkyl of 7-10 carbon atoms;
$R^5$, $R^6$, and $R^8$ are each, independently, alkyl of 1-6 carbon atoms, aralkyl of 7-10 carbon atoms, fluorenylmethyl, or phenyl which is optionally mono-, di-, or tri-substituted with a substituent selected from alkyl of 1-6 carbon atoms, alkoxy of 1-6 carbon atoms, hydroxy, cyano, halo, nitro, carbalkoxy of 2-7 carbon atoms, trifluoromethyl, amino, or a carboxylic acid;
m is 0-4;
n is 0-4;
p is 1-2;
q is 0-4;
r is 0-4;
wherein $R^3$, $R^4$, m, and n are independent in each of the $$[C(CH_2)_mCH(CH_2)_nN]$$
$$\phantom{[C(CH_2)_m}R^3\phantom{CH(CH_2)_n}R^4$$

subunits when p=2;
or a pharmaceutically acceptable salt thereof.
Of the compounds, preferred members are those in which m=0, n=0, and p=1; m=0, n=0, and p=2;

n=0, and $R^3$ is —$(CH_2)_qCO_2R^6$; m=0, n=0, and $R^3$ is —$(CH_2)_rNR^7CO_2R^8$; and m=0, n=0, and $R^3$ is hydrogen.

The pharmaceutically acceptable salts may be formed from inorganic cations such as sodium, potassium, and the like and organic acids such as, acetic, lactic, citric, tartaric, succinic, maleic, malonic, gluconic, and the like, when $R^3$ contains a basic amino group.

The compounds of this invention can be prepared by acylating rapamycin with an acylating agent having the general structure

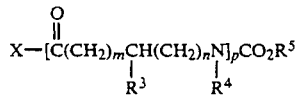

where X is OH in the presence of a coupling reagent, such as dicyclohexylcarbodiimide. The compounds of this invention also can be prepared using a mixed anhydride of the above described carboxylic acid as the acylating species. Alternatively, the acylating species can be an acid halide, where X can be Cl, Br, or I. The acylating groups used to prepare the compounds of this invention are commercially available or can be prepared by methods that are disclosed in the literature.

Immunosuppressive activity was evaluated in an in vitro standard pharmacological test procedure to measure lymphocyte proliferation (LAF) and in two in vivo standard pharmacological test procedures. The first in vivo procedure was a popliteal lymph node (PLN) test procedure which measured the effect of compounds of this invention on a mixed lymphocyte reaction and the second in vivo procedure evaluated the survival time of a pinch skin graft.

The comitogen-induced thymocyte proliferation procedure (LAF) was used as an in vitro measure of the immunosuppressive effects of representative compounds. Briefly, cells from the thymus of normal BALB/c mice are cultured for 72 hours with PHA and IL-1 and pulsed with tritiated thymidine during the last six hours. Cells are cultured with and without various concentrations of rapamycin, cyclosporin A, or test compound. Cells are harvested and incorporated; radioactivity is determined. Inhibition of lymphoproliferation is assessed in percent change in counts per minute from non-drug treated controls. The results are expressed by the following ratio, or as the percent inhibition of lymphoproliferation of 1 μM.

$$\frac{{}^3H\text{-control thymus cells} - H^3\text{-rapamycin-treated thymus cells}}{{}^3H\text{-control thymus cells} - H^3\text{-test compound-treated cells}}$$

A mixed lymphocyte reaction (MLR) occurs when lymphoid cells from genetically distinct animals are combined in tissue culture. Each stimulates the other to undergo blast transformation which results in increased DNA synthesis that can be quantified by the incorporation of tritiated thymidine. Since stimulating a MLR is a function of disparity at Major Histocompatibility antigens, an in vivo popliteal lymph node (PLN) test procedure closely correlates to host vs. graft disease. Briefly, irradiated spleen cells from BALB/c donors are injected into the right hind foot pad of recipient C3H mice. The drug is given daily, p.o. from Day 0 to Day 4. On Day 3 and Day 4, tritiated thymidine is given i.p., b.i.d. On Day 5, the hind popliteal lymph nodes are removed and dissolved, and radioactivity counted. The corresponding left PLN serves as the control for the PLN from the injected hind foot. Percent suppression is calculated using the non-drug treated animals as allogenic control. Rapamycin at a dose of 6 mg/kg, p.o. gave 86% suppression, whereas cyclosporin A at the same dose gave 43% suppression. Results are expressed by the following ratio:

$$\frac{{}^3H\text{-PLN cells control C3H mouse} - {}^3H\text{-PLN cells rapamycin-treated C3H mouse}}{{}^3H\text{-PLN cells control C3H mouse} - {}^3H\text{-PLN cells test compound-treated C3H mouse}}$$

The second in vivo test procedure is designed to determine the survival time of pinch skin graft from male DBA/2 donors transplanted to male BALB/c recipients. The method is adapted from Billingham R.E. and Medawar P.B., J. Exp. Biol. 28:385–402, (1951). Briefly, a pinch skin graft from the donor is grafted on the dorsum of the recipient as a homograft, and an autograft is used as control in the same region. The recipients are treated with either varying concentrations of cyclosporin A as test control or the test compound, intraperitoneally. Untreated recipients serve as rejection control. The graft is monitored daily and observations are recorded until the graft becomes dry and forms a blackened scab. This is considered as the rejection day. The mean graft survival time (number of days ±S.D.) of the drug treatment group is compared with the control group.

The following table summarizes the results of representative compounds of this invention in these three standard test procedures.

TABLE 1

| Compound | LAF* (ratio) | PLN* (ratio) | Skin Graft (days + SD) |
|---|---|---|---|
| Example 1 | 1.8 | 0.61 | 12.0 ± 1.6 |
| Example 2 | 0.33 | 0.62 | 11.5 ± 0.6 |
| Example 3 | 0.20 | + | 9.0 ± 0.9 |
| Example 4 | 4.9 | 0.18 | 12.3 ± 0.5 |
| Example 5 | 0.006 | + | 8.8 ± 0.9 |
| Example 6 | 5.4 | 0.33 | 11.5 ± 3.5 |
| Example 7 | 3% at 1 μM** | + | 7.7 ± 1.5 |
| Example 8 | 0.03 | 0.41 | + |
| Example 9 | 0.96 | 1.34 | 10.3 ± 0.8 |
| Example 10 | 2.0 | 0.96++ | 12.7 ± 1.2 |
| Example 11 | 0.004 | + | 10.5 ± 1.3 |
| Example 12 | 19.8 | −2.87 | 12.0 ± 2.0 |
| Example 13 | 22% at 1 μM** | + | 7.0 ± 0.6 |
| Rapamycin | 1.0 | 1.0 | 12.0 ± 1.7 |

*Calculation of ratios was described supra.
**Result expressed as percent inhibition of lymphoproliferation at 1 μM.
+ Not evaluated.
++Results obtained using cremophore/ethanol as a vehicle for administration. Ratios of 0.33 and 1.07 were also obtained using carboxymethyl cellulose as a vehicle for administration.

The results of these standard pharmacological test procedures demonstrate immunosuppressive activity both in vitro and in vivo for the compounds of this invention. Positive ratios in the LAF and PLN test procedures indicate suppression of T cell proliferation. As a transplanted pinch skin grafts are typically rejected within 6–7 days without the use of an immunosuppressive agent, the increased survival time of the skin graft when treated with the compounds of this invention further demonstrates their utility as immunosuppressive agents. While it appears that the compound disclosed by Example 12 may cause T cell proliferation in the PLN test procedure, it is believed a negative ratio in this test procedure coupled with an increased survival time observed in the skin graft test procedure indicates a proliferation of $T_{suppressor}$ cells, which are implicated in suppressing the immune response. (see, I. Roitt et al. Immunology, C. V. Moseby Co. 1989, p 12.8–12.11).

Antifungal activity of the compounds of this invention was measured against 5 strains of *Candida albicans* using a plate test procedure for measurement of inhibition. The following represents the typical procedure used. Compound to be tested was placed on sterile dried ¼" plate disks, and allowed to dry. Agar plates were seeded with fungi and allowed to solidify. The impregnated disks were placed on the seeded Agar surface and incubated for the time required for the particular culture. Results are expressed in MIC ($\mu$g/ml) to inhibit growth. The results of this test procedure showed that the compounds of this invention have antifungal activity; however, it was surprising that the compounds of this invention were less active than the parent compound, rapamycin.

TABLE 2*

| Compound | Strain of *Candida albicans* | | | | |
|---|---|---|---|---|---|
| | ATCC 10231 | ATCC 38246 | ATCC 38247 | ATCC 38248 | 3669 |
| Example 1 | >0.4 | >0.4 | >0.4 | >0.4 | >0.4 |
| Example 2 | 0.1 | 0.2 | 0.2 | 0.2 | 0.1 |
| Example 3 | 0.4 | >0.4 | >0.4 | >0.4 | 0.4 |
| Example 4 | 0.1 | 0.4 | 0.1 | 0.1 | 0.2 |
| Example 5 | >0.4 | >0.4 | >0.4 | >0.4 | >0.4 |
| Example 6 | 0.1 | >0.4 | 0.2 | 0.4 | >0.4 |
| Example 7 | + | + | + | + | + |
| Example 8 | >0.4 | >0.4 | >0.4 | >0.4 | >0.4 |
| Example 9 | 0.4 | >0.4 | 0.4 | >0.4 | >0.4 |
| Example 10 | 0.2 | >0.4 | 0.2 | 0.4 | 0.4 |
| Example 11 | >0.4 | >0.4 | >0.4 | >0.4 | >0.4 |
| Example 12 | 0.2 | >0.4 | 0.1 | 0.2 | 0.4 |
| Example 13 | >0.4 | >0.4 | >0.4 | >0.4 | >0.4 |
| Rapamycin | 0.003 | 0.025 | 0.003 | 0.006 | 0.025 |

*expressed as MIC ($\mu$g/ml)
+ not evaluated

Based on the results of these standard pharmacological test procedures, the compounds are useful in the treatment of transplantation rejection such as, heart, kidney, liver, bone marrow, and skin transplants; autoimmune diseases such as, lupus, rheumatoid arthritis, diabetes mellitus, myasthenia gravis, and multiple sclerosis; and diseases of inflammation such as, psoriasis, dermatitis, eczema, seborrhea, inflammatory bowel disease; and fungal infections.

The compounds may be administered neat or with a pharmaceutical carrier to a mammal in need thereof. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. The dosage to be used in the treatment must be subjectively determined by the attending physician.

In addition, the compounds of this invention may be employed as a solution, cream, or lotion by formulation with pharmaceutically acceptable vehicles containing 0.1–0.5 percent, preferably 2%, of active compound which may be administered to a fungally affected area.

The following examples illustrate the preparation of representative compounds of this invention.

EXAMPLE 1

Rapamycin-42-ester with N-[(1,1-dimethylethoxy)carbonyl]-glycylglycine

Under anhydrous conditions, a solution of rapamycin (3 g, 3.28 mmole) and N-[(1,1-dimethylethoxy)carbonyl]-glycylglycine (3.04 g, 13.1 mmole) in 40 mL of anhydrous dichloromethane was treated with dicyclohexylcarbodiimide (1.35 g, 6.56 mmole) followed by 4-dimethylaminopyridine (0.8 g, 6.56 mmole). After stirring at ambient temperature for 48 hours, the precipitated solid was collected and washed with dichloromethane. The combined filtrates were absorbed directly onto silica gel Merck 60 by adding the gel and evaporation to dryness. Flash chromatography of the preabsorbed material (using a gradient elution with ethylacetate-toluene from 2:1 to 1:0 v/v) afforded 1.05 g (28.3%) of the title compound isolated as a three quarter toluene solvate, along with the 31,42-diester of Example 2. HPLC analysis showed that the monoester is a 8.3:1 mixture of two conformers.

$^1$H NMR (CDCl$_3$, 400 MHz): δ1.46 (m, 9H, COO-Bu$^t$), 1.654 (s, 3H, CH$_3$C=C), 1.751 (s, 3H, CH$_3$C=C), 3.14 (s, 3H, CH$_3$O), 3.33 (s, 3H, CH$_3$O), 3.36 (s, 3H, CH$_3$O), 4.18 (d, 1H, CHOH), 4.75 (m, 1H, 42-CHO), 4.79 (s, 1H, OH); High Res. MS (neg. ion FAB) Calcd for C$_{60}$H$_{93}$N$_3$O$_{17}$: 1127.6504, measured mass 11.27.6474.

Anal. Calcd for C$_{60}$H$_{93}$N$_3$O$_{17}$.0.75 PhCH$_3$: C, 65.45; H, 8.33; N, 3.51; Found: C, 65,23; H, 8.32; N, 3.86.

The following representative compounds can be prepared from rapamycin and the appropriate terminally-N-substituted amino acid by employing the method used to prepare the title compound in Example 1.

Rapamycin-42-ester with N-[(fluorenylmethoxy)carbonyl]-alanylserine
Rapamycin-42-ester with N-[(fluorenylmethoxy)carbonyl]-glycylglycine
Rapamycin-42-ester with N-[(ethoxy)carbonyl]-arginylmethionine
Rapamycin-42-ester with N-[(4'-chlorophenoxy)carbonyl]-histidylarginine
Rapamycin-42-ester with N-[(phenoxy)carbonyl]-tryptophanylleucine
Rapamycin-42-ester with N-[(phenylmethoxy)carbonyl]-N-methylglycyl-N-ethylalanine
Rapamycin-42-ester with N-[(phenylmethoxy)carbonyl]-N-methyl-β-alanylphenylalanine
Rapamycin-42-ester with N-[(1,1-dimethylethoxy)carbonyl]-cysteinylglycine

EXAMPLE 2

Rapamycin-31,42-diester with N-[(1,1-dimethylethoxy)carbonyl]-glycylglycine

The title compound (1.85 g, 42%) was separated from the 42-monoester as described in Example 1 and isolated as a three quarter toluene solvate. HPLC analysis showed that the diester is a 8.1:1 mixture of conformers.

$^1$H NMR (CDCl$_3$, 400 MHz): δ1.452 (m, 18H, COO-Bu$^t$), 1.6612 (s, 3H, CH$_3$C=C), 1.7815 (s, 3H, CH$_3$C=C), 3.14 (s, 3H, OCH$_3$), 3.34 (s, 3H, OCH$_3$), 3.35 (s, 3H, OCH$_3$), 4.52 (s, 1H, OH), 4.79 (m, 1H, 42-CHO); High Res. MS (neg. ion FAB): Calcd for C$_{69}$H$_{107}$N$_5$O$_{21}$ 1341.7458, measured mass: 1341.7463.

Anal. Calcd for C$_{69}$H$_{107}$N$_5$O$_{21}$.0.75 PhCH$_3$: C, 63.17; H, 8.06; N, 4.96; Found: C, 62.83; H, 8.09; N, 5.00.

The following representative compounds can be prepared from rapamycin and the appropriate terminally-N-substituted amino acid by employing the method used to prepare the title compound in Example 2.

Rapamycin-31,42-diester with N-[(fluorenylmethoxy)carbonyl]-alanylserine
Rapamycin-31,42-diester with N-[(fluorenylmethoxy)carbonyl]-glycylglycine
Rapamycin-31,42-diester with N-[(ethoxy)carbonyl]-arginylmethionine
Rapamycin-31,42-diester with N-[(4'-chlorophenoxy)carbonyl]-histidylarginine*
Rapamycin-31,42-diester with N-[(phenoxy)carbonyl]-tryptophanylleucine
Rapamycin-31,42-diester with N-[(phenylmethoxy)carbonyl)]-N-methylglycyl-N-ethyl-alanine
Rapamycin-31,42-diester with N-[(phenylmethoxy)carbonyl]-N-methyl-β-alanylphenyl-alanine
Rapamycin-31,42-diester with N-[(1,1-dimethylethoxy)carbonyl]-cysteinylglycine

EXAMPLE 3

Rapamycin-31,42-diester with N-[(1,1-dimethylethoxy)carbonyl]-N-methylglycine Under anhydrous conditions, an ice cold solution of rapamycin (2 g, 2.18 mmole) and N$^α$-Boc sarcosine (1.65 g, 8.75 mmole) in 20 ml of anhydrous dichloromethane was treated with dicyclohexylcarbodiimide (1.8 g, 8.7 mmole) followed by 4-dimethylaminopyridine (1 g, 8.7 mmole). After stirring overnight at ambient temperature, the precipitated solid was collected and washed with dichloromethane. The combined filtrates were evaporated to dryness to give an amorphous amber solid (3 g). The crude product was purified by flash chromatography (on silica Merck 60, elution with hexane-ethylacetate 1:1, v/v) to provide the title compound (0.75 g, 27.4%) along with the 42-monoester of Example 4. HPLC analysis showed that the diester is a 19.8:1 mixture of two conformers. The multiplicity of the NMR peaks suggests the presence of amide rotamers.

$^1$H NMR (CDCl$_3$, 400 MHz): δ1.411, 1.438, 1.448 and 1.474 (m, 18H, COOBu$^t$), 2.91 (m, 6H, NCH$_3$), 3.14 (s, 3H, CH$_3$O), 3.34 (s, 3H, CH$_3$O), 3.37 (s, 3H, CH$_3$O), 4.73 (broad, 1H, 42-CHO), 4.82 (2s, 1H, OH); High Res. MS (neg. ion FAB): Calcd. for C$_{67}$H$_{105}$N$_3$O$_{19}$ 1255.7342, measured mass 1255.7289.

Anal. Calcd for C$_{67}$H$_{105}$N$_3$O$_{19}$: C, 64.04; H, 8.42; N, 3.34; Found: C, 64.14; H, 8.74; N, 3.63.

The following representative compounds can be prepared from rapamycin and the appropriate terminally-N-substituted amino acid by employing the method used to prepare the title compound in Example 3.

Rapamycin-31,42-diester with N-[(ethoxy)carbonyl]-tyrosine
Rapamycin-31,42-diester with N-[(fluorenylmethoxy)carbonyl]-phenylalanine
Rapamycin-31,42-diester with N-[(3',4',5'-trihydroxyphenoxy)carbonyl]-isoleucine
Rapamycin-31,42-diester with N-[(1,1-dimethylethoxy)carbonyl]-glutamine
Rapamycin-31,42-diester with N-[(phenoxy)carbonyl]-N-methylalanine
Rapamycin-31,42-diester with N-[(propyloxy)carbonyl]-4-aminobutyric acid
Rapamycin-31,42-diester with N-[(phenylmethoxy)carbonyl]-7-aminoheptanoic acid
Rapamycin-31,42-diester with N-[(fluorenylmethoxy)carbonyl]-serine

EXAMPLE 4

Rapamycin-42-ester with N-[(1,1-dimethylethoxy)carbonyl]-N-methylglycine

Under anhydrous conditions, an ice cold solution of rapamycin (0.95 g, 1.02 mmole) and N$^α$-Boc sarcosine (0.21 g, 1.1 mmole) in 20 mL of anhydrous dichloromethane was treated with dicyclohexylcarbodiimide 0.21 g, 1 mmole) followed by 4-dimethylaminopyridine (0.12 g, 1 mmole). After stirring for 4 hours at ambient temperature, the precipitated solid was collected and washed with dichloromethane. The combined filtrates were concentrated in vacuo to give an amorphous amber solid. Flash chromatography of the crude product (on silica Merck 60, elution with hexaneethylacetate 1:1 v/v to remove the diester of Example 3, followed by chloroformethylacetate-methanol 75:25:1 v/v) provided partially purified title compound (0.38 g, 35%).

Pure product was obtained by preparative HPLC (Waters Prep 500, silica gel, chloroform-ethylacetate-methanol 75:25:1 v/v, flow rate 250 mL/min). HPLC analysis showed that the ester is a 6.6:1 mixture of two conformers. The multiplicity of NMR peaks suggests the presence of amide rotamers.

$^1$H NMR (CDCl$_3$, 400 MHz): δ1.42–1.46 (ds, 9H, COOBu$^t$), 2.91 (ds, 3H, NCH$_3$), 1.644 (s, 3H, CH$_3$C=C), 1.738 (s, 3H, CH$_3$C=C), 3.12 (s, 3H, CH$_3$O), 3.32 (s, 3H, CH$_3$O), 3.35 (s, 3H, CH$_3$O), 4.18 (d, 1H, CHOH), 4.71 (broad, 1H, 42-CHO), 4.78 (broad s, 1H, OH); High Res. MS (neg. ion FAB): Calcd for C$_{59}$H$_{92}$N$_2$O$_{16}$ 1084.6446, measured mass 1084.6503.

Anal. Calcd for C$_{59}$H$_{92}$N$_2$O$_{16}$: C, 65.29; H, 8.54; N, 2.58; Found: C, 65.25; H, 8.52; N, 2.42.

The following representative compounds can be prepared from rapamycin and the appropriate terminally-N-substituted amino acid by employing the method used to prepare the title compound in Example 4.

Rapamycin-42-ester with N-[(ethoxy)carbonyl]-tyrosine

Rapamycin-42-ester with N-[(fluorenylmethoxy)carbonyl]-phenylalanine

Rapamycin-42-ester with N-[(3',4',5'-trihydroxyphenoxy)carbonyl]-isoleucine

Rapamycin-42-ester with N-[(1,1-dimethylethoxy)carbonyl]-glutamine

Rapamycin-42-ester with N-[(phenoxy)carbonyl]-N-methylalanine

Rapamycin-42-ester with N-[(propyloxy)carbonyl]-4-aminobutryic acid

Rapamycin-42-ester with N-[(phenylmethoxy)carbonyl]-7-aminoheptanoic acid

Rapamycin-31,42-diester with N-[(fluorenylmethoxy)carbonyl]serine

EXAMPLE 5

Rapamycin-31,42-diester with 5-(1,1-dimethylethoxy)-2-[[(1,1-dimethylethoxy)carbonyl]amino]-5-oxopentanoic acid Under anhydrous conditions, an ice cold solution of rapamycin (4 g, 4.37 mmole) and L-glutamic acid N$^\alpha$-Boc-γ-tert-butylester (4.9 g, 16.1 mmole) in 40 mL of dry dichloromethane was treated with dicyclohexylcarbodiimide (1.8 g, 8.7 mmole) followed by 4-dimethylaminopyridine (1 g, 8.7 mmole). After stirring overnight at room temperature, the precipitated solid was collected and washed with dichloromethane. The combined filtrates were concentrated in vacuo to provide 11 g of an amorphous amber solid. The crude product was purified by flash chromatography (on silica Merck 60, gradient elution with hexane-ethylacetate from 2:1 to 1:1, v/v) to yield 4.52 g (69.6%) of the title compound along with the 42-monoester of Example 6. HPLC analysis showed that the diester consists of a 6.6:1 mixture of two conformers.

$^1$H NMR (CDCl$_3$, 400 MHz): δ1.42 (m, 36H, COOBu$^t$), 1.646 (s, 3H, CH$_3$C=C), 1.701 (s, 3H, CH$_3$C=C), 3.13 (s, 3H, CH$_3$O), 3.34 (s, 3H, CH$_3$O), 3.36 (s, 3H, CH$_3$O), 4.735 (m, 2H, OH+42-CH—O); High Res. MS (neg. ion FAB): calc. for C$_{79}$H$_{125}$N$_3$O$_{23}$ 1483.8715, measured mass 1483.8714.

Anal. Calcd for C$_{79}$H$_{125}$N$_3$O$_{23}$: C, 63.90; H, 8.49; N, 2.83; Found: C, 63.63; H, 8.41; N, 2.44.

The following representative compounds can be prepared from rapamycin and the appropriately terminally-N-substituted amino diacid monoester by employing the method used to prepare the title compound in Example 5.

Rapamycin-31,42-diester with 6-(phenylmethoxy)-2-[[fluorenylmethoxy)carbonyl]amino]-6-oxohexanoic acid Rapamycin-31,42-diester with 6-(4'-methylphenoxy)-3-[[(phenylmethoxy)carbonyl]amino-6-oxohexanoic acid Rapamycin-31,42-diester with 6-(ethoxy)-4-[[(phenoxy)carbonyl]amino]-6-oxohexanoic acid Rapamycin-31,42-diester with 6-(methoxy)-5-[[(ethoxy)carbonyl]amino]-6-oxohexanoic acid Rapamycin-31,42-diester with 4-(phenoxy)-2-[N-[(1,1-dimethylethoxy)carbonyl]-N-methylamino]-4-oxobutanoic acid Rapamycin-31,42-diester with 4-(phenylmethoxy)-3-[N-[(methoxy)carbonyl]-N-methylamino]-4-oxobutanoic acid

EXAMPLE 6

Rapamycin-42-ester with 5-(1,1-dimethylethoxy)-2-[[(1,1-dimethylethoxy)carbonyl]amino]-5-oxopentanoic acid The title compound (1.14 g, 20.6%) was separated from the 31,42-diester as described in Example 5 and isolated as the quarter hydrate/mono-ethyl acetate solvate. HPLC analysis showed that the monoester is a 11.5:1 mixture of two conformers.

$^1$H NMR (CDCl$_3$, 400 MHz): δ1.425 (m, 18H, COOBu$^t$), 1.643 (s, 3H, CH$_3$C=C), 1.737 (s, 3H, CH$_3$C=C), 3.13 (s, 3H, CH$_3$O), 3.32 (s, 3H, CH$_3$O), 3.36 (s, 3H, CH$_3$O), 4.17 (d, 1H, CHOH), 4.71 (M, 1H, 42-CHO), 4.785 (s, 1H, OH); High Resolution MS (neg. ion FAB): Calc. for C$_{65}$H$_{102}$N$_2$O$_{18}$ 1198.7127, measured mass 1198.7077.

Anal. Calcd for C$_{65}$H$_{102}$N$_2$O$_{18}$·CH$_3$COOEt·0.25 H$_2$O: C, 64.13, H, 8.60; N, 2.17; Found: C, 64.18; H, 8.52: N, 2.01.

The following representative compounds can be prepared from rapamycin and the appropriately terminally-N-substituted amino diacid monoester by employing the method used to prepare the title compound in Example 6.

Rapamycin-42-ester with 6-(phenylmethoxy)-2-[[fluorenylmethoxy)carbonyl]-amino]-6-oxohexanoic acid Rapamycin-42-ester with 6-(4'-methylphenoxy)-3-[[(phenylmethoxy)carbonyl]-amino-6-oxohexanoic acid Rapamycin-42-iester with 6-(ethoxy)-4-[[(phenoxy)carbonyl]amino]-6-oxo-hexanoic acid Rapamycin-42-ester with 6-(methoxy)-5-[[(ethoxy)carbonyl]amino]-6-oxo-hexanoic acid Rapamycin-42-ester with 4-(phenoxy)-2-[N-[(1,1-dimethylethoxy)carbonyl]-N-methylamino]-4-oxobutanoic acid Rapamycin-42-ester with 4-(phenylmethoxy)-3-[N-[(methoxy)carbonyl]-N-methylamino]-4-oxobutanoic acid

EXAMPLE 7

Rapamycin-31,42-diester with 2-[[(1,1-dimethylethoxy)carbonyl]amino]-4-oxo-4-(phenylmethoxy) butanoic acid Under anhydrous conditions, 295 mg (1.21 mmol) of 2,4,6 trichlorobenzoyl chloride was added to a solution of 391 mg (1.21 mmol) of N$^\alpha$-Boc-L-aspartic acid-β- benzyl ester and 170 μL (1.21 mmol) of Et$_3$N in 1 mL of THF at room temperature. After stirring for 30 minutes, 500 mg (0.55 mmol) of rapamycin and 295 mg (2.42 mmol) of dimethylaminopyridine was added and the reaction was left to stir overnight. The reaction mixture was then filtered and the filtrate concentrated in vacuo. Pure product (200 mg, 25%) was obtained by preparative HPLC (5 cm column, 40% ethyl acetate-hexane). The product was isolated as the heptahydrate.

$^1$H NMR (CDCl$_3$, 400 MHz) δ7.347 (s, 10H, Ar), 6.223, 5.126 (s, 4H, CH$_2$Ph), 4.698 (m, 1H, CH—CO$_2$), 4.587 (m, 2H, NH), 3.353 (s, 3H, CH$_3$O), 3.337 (s, 3H, CH$_3$O), 3.301 (s, 3H, CH$_3$O), 2.775 (m, 4H, CH$_2$CO$_2$); IR (KBr) 3420 (OH), 2935 (CH), 2920 (CH), 1730 (C=O), 1650, 1500, 1455, 1370, 1170 cm$^{-1}$; MS (neg. ion FAB) 1523 (M$^-$), 1433, 297, 248, 205, 148, 44, 25 (100).

Anal. Calcd for C$_{83}$H$_{117}$N$_3$O$_{23}$.7H$_2$O C, 60.40; H, 7.09; N, 2.54; Found: C, 60.54; H, 7.28; N, 2.56.

EXAMPLE 8

Rapamycin-31,42-diester with 3-[[(1,1-dimethylethoxy)carbonyl]amino]-4-oxo-4-(phenylmethoxy) butanoic acid Under anhydrous conditions, 532 mg (2.18 mmol) of 2,4,6 trichlorobenzoyl chloride in 1 mL THF was added to a solution of 704 mg (2.18 mmol) of N$^α$-Boc-L-aspartic acid-α-benzyl ester and 303 μL (2.18 mmol) of Et$_3$N in 5 mL of THF at room temperature. After stirring for 20 minutes, the reaction mixture was filtered over sintered glass, and the precipitate was washed with THF. The filtrate was concentrated in vacuo to give a thick oil. The oil was dissolved in 5 mL of benzene and 1.00 g (1.09 mmol) of rapamycin and 532 mg (4.36 mmol) of dimethylaminopyridine in 1 mL of benzene was added dropwise. The reaction was stirred for 2 hr, poured into ethyl acetate, and washed consecutively with 0.5N HCl and brine. The solution was dried over sodium sulfate, decanted, concentrated in vacuo to give a white foamy solid, which was purified via flash chromatography on a 60 mm × 100 mm silica column (20–40% ethyl acetate/hexane as eluant) to give 532 mg (33%) of the title compound which was isolated as the hydrate.

$^1$H NMR (CDCl$_3$, 400 MHz) δ7.362 (s, 10H, Ar), 5.193 (s, 4H, CH$_2$Ph), 4.596·(m, 1H, CH—CO$_2$), 4.586 (m, 2H, NH), 3.336 (s, 3H, CH$_3$O), 3.306 (s, 3H, CH$_3$O), 3.145 (s, 3H, CH$_3$O); IR (KBr) 3410 (OH), 2950 (CH), 2920 (CH), 1735 (C=O), 1710 (C=O), 1640, 1490, 1445, 1350, 1150 cm$^{-1}$; MS (neg. ion FAB) 1524 (M$^-$), 1434, 297, 248, 232, 214, 205, 167, 148, 42 (100), 26.

Anal. Calcd for C$_{83}$H$_{117}$N$_3$O$_{23}$.H$_2$O: C, 65.38; H, 7.73; N, 2.76; Found: C, 64.85; H, 7.67; N, 2.56.

EXAMPLE 9

Rapamycin-42-ester with 3-[[(1,1-dimethylethoxy)carbonyl]amino]-4-oxo-4-(phenylmethoxy) butanoic acid The title compound (374 mg, 23%) was prepared by the method described in the previous Example and separated from the compound described in the previous Example by flash chromatography (20–40% ethyl acetate/hexane as the eluant) and isolated as the sesquihydrate.

$^1$H NMR (CDCl$_3$, 400 MHz) δ7.356 (s, 5H, Ar), 5.185 (s, 2H, CH$_2$Ph), 4.635 (m, 1H, CH-CO$_2$), 4.582 (m, 1H, NH), 3.330 (s, 6H, CH$_3$O), 3.135 (s, 3H, CH$_3$O); IR (KBr) 3410 (OH), 2950 (CH), 2920 (CH), 1735 (C=O), 1710 (C=O), 1640, 1490, 1445, 1350, 1150 cm$^{-1}$; MS (neg. ion FAB) 1218 (M$^-$), 1127, 590, 168, 42, 25, 17 (100).

Anal. Calcd for C$_{67}$H$_{98}$N$_2$O$_{18}$. 1.5 H$_2$O: C, 63.64; H, 8.21; N, 2.22; Found: C, 63.64; H, 7.51; N, 2.13.

EXAMPLE 10

Rapamycin-42-ester with 5-(1,1-dimethyloxy)-4-[[(1,1-dimethylethoxy)carbonyl]amino]-5-oxopentanoic acid Under anhydrous conditions, an ice cold solution of rapamycin (4 g, 4.37 mmole) and L-glutamic acid N$^α$-Boc-α-tert-butylester (4.9 g, 16.1 mmole) in 40 mL of anhydrous dichloromethane was treated with dicyclohexylcarbodiimide (1.8 g, 8.7 mmole) followed by 4-dimethylamino pyridine (1 g, 8.7 mmole). After stirring overnight at ambient temperature, the precipitated solid was collected and washed with dichloromethane. The combined filtrates were concentrated in vacuo to give 9 g of an amorphous amber solid. The crude product was purified by flash chromatography (on silica Merck 60, gradient elution with hexane-ethylacetate from 2:1 to 3:2, v/v) to provide 1.35 g (25.7%) of the title compound along with the 31,42-diester of Example 11. HPLC analysis showed that the monoester is a 7.5:1 mixture of two conformers.

$^1$H NMR (CDCl$_3$, 400 MHz): δ1.43 (s, 9H, COOBu$^t$) and 1.46 (s, 9H, COOBu$^t$), 1.65 (s, 3H, CH$_3$C=C), 1.75 (s, 3H, CH$_3$C=C), 3.14 (s, 3H, CH$_3$O), 3.34 (s, 3H, CH$_3$O), 3.38 (s, 3H, CH$_3$O), 4.18 (d, 1H, CH-OH), 4.65 (m, 1H, 42-CHO), 4.80 (s, 1H, OH); High Res. MS (neg. ion FAB). Calc. for C$_{65}$H$_{102}$N$_2$O$_{18}$: 1198.7126, measured mass 1198.7135.

Anal. Calcd for C$_{65}$H$_{102}$N$_2$O$_{18}$: C, 65.09; H, 8.57; N, 2.34; Found C, 65.04; H, 8.33; N, 2.64.

EXAMPLE 11

Rapamycin-31,42-diester with 5-(1,1-dimethylethoxy)-4-[[(1,1-dimethylethoxy)-carbonyl]-amino]-5-oxopentanoic acid The title compound was prepared (0.83 g, 12.8%) along with the 42-monoester as described in Example 10. HPLC analysis showed that the diester is a 7.7:1 mixture of two conformers.

$^1$H NMR (CDCl$_3$, 400 MHz): δ1.43 (s, 18H, COOBu$^t$), 1.46 (s, 18H, COOBu$^t$), 1.659 (s, 3H, CH$_3$C=C), 1.759 (s, 3H, CH$_3$C=C), 3.14 (s, 3H, CH$_3$O), 3.34 (s, 3H, CH$_3$O), 3.38 (s, 3H, CH$_3$O), 4.66 (m, 1H, 42-CHO), 4.72 (s, 1H, OH); High Res. MS (neg. ion FAB): Calcd for C$_{79}$H$_{125}$N$_3$O$_{23}$: 1483.8704, measured mass 1483.8636.

Anal. Calcd for C$_{79}$H$_{125}$N$_3$O$_{23}$: C, 63.90; H, 8.49; N, 2.83; Found: C, 63.68; H, 8.60; N, 3.20.

EXAMPLE 12

Rapamycin-42-ester with N$^α$, N$^ε$-bis[(1,1-dimethylethoxy)carbonyl]-L-lysine Under anhydrous conditions, a solution of rapamycin (3 g, 3.28 mmole) and N$^α$, N$^ε$-bis-Boc-L-lysine (4.5 g, 13 mmole) in 40 mL of anhydrous dichloromethane was treated with dicyclohexylcarbodiimide (1.35 g, 6.56 mmole) followed by 4-dimethylaminopyridine (0.8 g, 6.56 m mole). After stirring overnight at ambient temperature, the precipitated solid was collected and washed with dichloromethane. The combined filtrates were concentrated in vacuo to give an amorphous amber solid. Flash chromatography of the crude product (on silica Merck 60, elution with hexane-ethylacetate 1:1 v/v) gave partially purified title compound. Pure product (0.8 g, 19.6%) was obtained by preparative HPLC (Waters Prep 500, silica gel, hexane-ethylacetate 3:2 v/v, flow rate 250 mL/min). HPLC analysis showed that the monoester is a 9:1 mixture of two conformers.

$^1$H NMR (CDCl$_3$, 400 MHz): δ1.438 (m, 9H, COO-Bu$^t$), 1.455 (s, 9H, COOBu$^t$), 1.652 (s, 3H, CH$_3$C=C), 1.752 (s, 3H, CH$_3$C=C), 3.14 (s, 3H, CH$_3$O), 3.33(s, 3H, CH$_3$O), 3.37 (s, 3H, CH$_3$O), 4.18 (d, 1H, CHOH), 4.72 (m, 1H, 42-CHO), 4.79 (s, 1H, OH); High Res. MS (neg. ion FAB): Calcd for C$_{67}$H$_{107}$N$_3$O$_{18}$: 1241.7549, measured mass 1241.7604.

Anal. Calcd for C$_{67}$H$_{107}$N$_3$O$_{18}$: C, 64.76; H, 8.68; N, 3.38; Found: C, 64.58; H, 9.01; N, 3.10.

EXAMPLE 13

Rapamycin-31,42-diester with N$^\alpha$, N$^\epsilon$bis [(1,1-dimethylethoxy)carbonyl]-L-lysine Under a nitrogen atmosphere, a solution of N$^\alpha$, N$^\epsilon$bis-Boc-L-lysine (1.038 g, 3 mmole) and triethylamine (0.42 mL, 3 mmmole) in 10 mL of anhydrous THF was treated in one portion with 2,4,6-trichlorobenzoyl chloride (0.73 g, 3 mmole). After stirring for 20 minutes at ambient temperature, the precipitated solid was collected and the filtrate was concentrated in vacuo. The resulting mixed anhydride was dissolved in 5 mL of benzeme and added to a stirred solution of rapamycin (1 g, 1.09 mmole) containing 4-dimethylamino pyridine (0.59 g, 4.8 mmoles) in 10 mL of benzene. After stirring at ambient temperature overnight, the precipitated solid was collected and the filtrate was evaporated to dryness (yellow foam). The crude product was purified by flash chromatography (on silica Merck 60, elution with hexane-ethylacetate 1:1) to provide title compound (1.15 g, 67%). HPLC analysis shows that the diester is a 9:1 mixture of two conformers.

$^1$H NMR (CDCl$_3$, 400 MHz): δ1.426 (m, 9H, COO-Bu$^t$), 1.438 (s, 9H, COOBu$^t$), 1.443 (s, 9H, COOBu$^t$), 1.446 (s, 9H, COOBu$^t$), 3.141 (s, 3H, CH$_3$O), 3.36 (s, 3H, CH$_3$O), 3.378 (s, 3H, CH$_3$O), 4.68–4.76 (m, 2H, OH and 42-CHO); High res. MS (neg. ion FAB): Calcd. for C$_{83}$H$_{135}$N$_5$O$_{23}$ 1569.9526, measured mass 1569.9537.

Anal. Calcd. for C$_{83}$H$_{135}$N$_5$O$_{23}$: C, 63.46; H, 8.66; N, 4.46; Found: C, 63.06; H, 8.84; N, 4.09.

What is claimed is:

1. A compound of the formula wherein R$^1$ and R$^2$ are each, independently, hydrogen or $$-[\overset{O}{\overset{\|}{C}}(CH_2)_m\underset{R^3}{\overset{}{C}H}(CH_2)_n\underset{R^4}{\overset{}{N}}]_pCO_2R^5$$

with the proviso that R$^1$ and R$^2$ are not both hydrogen;

R$^3$ is hydrogen, alkyl of 1–6 carbon atoms, phenylalkyl of 7–10 carbon atoms, —(CH$_2$)$_q$CO$_2$R$^6$, —(CH$_2$)$_r$NR$^7$CO$_2$R$^8$, carbamylalkyl of 2–3 carbon atoms, aminoalkyl of 1–4 carbon atoms, hydroxyalkyl of 1–4 carbon atoms, guanylalkyl of 2–4 carbon atoms, mercaptoalkyl of 1–4 carbon atoms, alkylthioalkyl of 2–6 carbon atoms, indolylmethyl, hydroxyphenylmethyl, imidazolylmethyl or phenyl which is optionally mono-, di-, or tri-substituted with a substitutent selected from alkyl of 1–6 carbon atoms, alkoxy of 1–6 carbon atoms, hydroxy, cyano, halo, nitro, carbalkoxy of 2–7 carbon atoms, trifluoromethyl, amino, or —CO$_2$H, R$^4$ and R$^7$ are each, independently, hydrogen, alkyl of 1–6 carbon atoms, or phenylaklyl of 7–10 carbon atoms;

R$^5$, R$^6$, and R$^8$ are each, independently, alkyl of 1–6 carbon atoms, phenylalk of 7–10 carbon atoms, fluorenylmethyl, or phenyl which is optionally mono-, di-, or tri-substituted with a substituent selected from alkyl of 1–6 carbon atoms, alkoxy of 1–6 carbon atoms, hydroxy, cyano, halo, nitro, carbalkoxy of 2–7 carbon atoms, trifluoromethyl, amino, or —CO$_2$H;

m is 0–4;
n is 0–4;
p is 1–2;
q is 0–4;
r is 0–4;

wherein R$^3$, R$^4$, m, and n are independent in each of the $$[\overset{O}{\overset{\|}{C}}(CH_2)_m\underset{R^3}{\overset{}{C}H}(CH_2)_n\underset{R^4}{\overset{}{N}}]$$

subunits when p=2; or a pharmaceutically acceptable salt thereof.

2. A compound of claim 1 where m=0, n=0, and p=1 or a pharmaceutically acceptable salt thereof.

3. A compound of claim 1 where m=0, n=0, and p=2 or a pharmaceutically acceptable salt thereof.

4. A compound of claim 1 where n=0, and R$^3$ is —(CH$_2$)$_q$CO$_2$R$^6$ or a pharmaceutically acceptable salt thereof.

5. A compound of claim 1 where m=0, n=0, and R$^3$ is —(CH$_2$)$_r$NR$^7$CO$_2$R$^8$ or a pharmaceutically acceptable salt thereof.

6. A compound of claim 1 where m=0, n=0, and R$^3$ is hydrogen or a pharmaceutically acceptable salt thereof.

7. A compound of claim 1 which is rapamycin-42-ester with N-[(1,1-dimethylethoxy)carbonyl]-glycylglycine or a pharmaceutically acceptable salt thereof.

8. A compound of claim 1 which is rapamycin-31,42-diester with N-[(1,1-dimethyl-ethoxy)carbonyl]- glycylglycine or a pharmaceutically acceptable salt thereof.

9. A compound of claim 1 which is rapamycin-31,42-diester with N-[(1,1-dimethylethoxy)carbonyl]-N-methylglycine or a pharmaceutically acceptable salt thereof.

10. A compound of claim 1 which is rapamycin-42-ester with N-[(1,1-dimethylethoxy)carbonyl]-N-methylglycine or a pharmaceutically acceptable salt thereof.

11. A compound of claim 1 which is rapamycin-31,42-diester with 5-(1,1-dimethylethoxy)-2-[[(1,1-dimethylethoxy)carbonyl]amino]-5-oxopentanoic acid or a pharmaceutically acceptable salt thereof.

12. A compound of claim 1 which is rapamycin-42-ester with 5-(1,1-dimethylethoxy)-2- [[(1,1-dimethylethoxy)carbonyl]amino]-5-oxopentanoic acid or a pharmaceutically acceptable salt thereof.

13. A compound of claim 1 which is rapamycin-31,42-diester with 2-[[(1,1-dimethylethoxy)carbonyl]amino]-4-oxo-4-(phenylmethoxy) butanoic acid or a pharmaceutically acceptable salt thereof.

14. A compound of claim 1 which is rapamycin-31,42-diester with 3-[[(1,1-dimethylethoxy)carbonyl]amino]-4-oxo-4-(phenylmethoxy) butanoic acid or a pharmaceutically acceptable salt thereof.

15. A compound of claim 1 which is rapamycin-42-ester with 3-[[(1,1-dimethylethoxy)carbonyl]amino]-4-oxo-4-(phenylmethoxy) butanoic acid or a pharmaceutically acceptable salt thereof.

16. A compound of claim 1 which is rapamycin-42-ester with 5-(1,1-dimethyloxy)-4-[[(1,1-dimethylethoxy)carbonyl]amino]-5-oxopentanoic acid or a pharmaceutically acceptable salt thereof.

17. A compound of claim 1 which is rapamycin-31,42-diester with 5-(1,1-dimethylethoxy)-4-[[(1,1-dimethylethoxy)carbonyl]amino]-5-oxopentanoic acid or a pharmaceutically acceptable salt thereof.

18. A compound of claim 1 which is rapamycin-42-ester with $N^\alpha$, $N^\epsilon$-bis[(1,1-dimethylethoxy)carbonyl]-L-lysine or a pharmaceutically acceptable salt thereof.

19. A compound of claim 1 which is rapamycin-31,42-diester with $N^\alpha$, $N^\epsilon$-bis[(1,1-dimethylethoxy)carbonyl]-L-lysine or a pharmaceutically acceptable salt thereof.

20. A method of treating transplantation rejection, host vs. graft disease, autoimmune diseases, and diseases of inflammation in a mammal by administering an effective amount of a compound having the formula

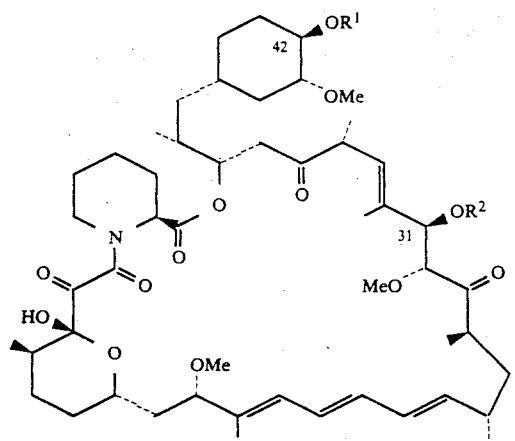

wherein $R^1$ and $R^2$ are each, independently, hydrogen or

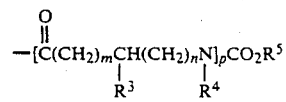

with the proviso that $R^1$ and $R^2$ are not both hydrogen;
$R^3$ is hydrogen, alkyl of 1-6 carbon atoms, phenylalkyl of 7-10 carbon atoms, $-(CH_2)_qCO_2R^6$, $-(CH_2)_rNR^7CO_2R^8$, carbamylalkyl of 2-3 carbon atoms, aminoalkyl of 1-4 carbon atoms, hydroxyalkyl of 1-4 carbon atoms, guanylalkyl of 2-4 carbon atoms, mercaptoalkyl of 1-4 carbon atoms, alkylthioalkyl of 2-6 carbon atoms, indolylmethyl, hydroxyphenylmethyl, imidazoylmethyl or phenyl which is optionally mono-, di-, or tri-substituted with a substituent selected from alkyl of 1-6 carbon atoms, alkoxy of 1-6 carbon atoms, hydroxy, cyano, halo, nitro, carbalkoxy of 2-7 carbon atoms, trifluoromethyl, amino, or $-CO_2H$;
$R^4$ and $R^7$ are each, independently, hydrogen, alkyl of 1-6 carbon atoms, or phenylalkyl of 7-10 carbon atoms;
$R^5$, $R^6$, and $R^8$ are each, independently, alkyl of 1-6 carbon atoms, phenylalkyl of 7-10 carbon atoms, fluorenylmethyl, or phenyl which is optionally mono-, di-, or trisubstituted with a substituent with a substituent selected from alkyl of 1-6 carbon atoms, alkoxy of 1-6 carbon atoms, hydroxy, cyano, halo, nitro, carbalkoxy of 2-7 carbon atoms, trifluoromethyl, amino, or $-CO_2H$;
m is 0-4;
n is 0-4;
p is 1-2;
q is 0-4;
r is 0-4;
wherein $R^3$, $R^4$, m, and n are independent in each of the

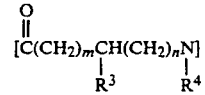

subunits when p=2;
or a pharmaceutically acceptable salt thereof.

21. A pharmaceutical composition for use as an immunosuppressive agent comprising an immunosuppressive amount of a compound of claim 1 or a pharmaceutically acceptable salt thereof.

22. A composition in claim 21 in unit dosage form.

* * * * *